(12) United States Patent
Ludwin et al.

(10) Patent No.: US 9,375,163 B2
(45) Date of Patent: Jun. 28, 2016

(54) LOCATION SENSING USING A LOCAL COORDINATE SYSTEM

(71) Applicant: BIOSENSE WEBSTER (ISRAEL), LTD., Yokneam (IL)

(72) Inventors: Doron Moshe Ludwin, Haifa (IL); Aharon Turgeman, Zichron Ya'acov (IL); Eliahu Zino, Atlit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 525 days.

(21) Appl. No.: 13/687,079

(22) Filed: Nov. 28, 2012

(65) Prior Publication Data
US 2014/0148688 A1    May 29, 2014

(51) Int. Cl.
| | |
|---|---|
| *A61B 5/05* | (2006.01) |
| *A61B 5/06* | (2006.01) |
| *A61M 5/00* | (2006.01) |
| *A61B 5/00* | (2006.01) |
| *A61B 19/00* | (2006.01) |
| *A61B 17/00* | (2006.01) |

(52) U.S. Cl.
CPC . *A61B 5/062* (2013.01); *A61B 5/44* (2013.01); *A61B 19/5244* (2013.01); *A61M 5/00* (2013.01); *A61B 5/6859* (2013.01); *A61B 2017/00243* (2013.01); *A61B 2017/00292* (2013.01); *A61B 2017/00703* (2013.01); *A61B 2017/00951* (2013.01); *A61B 2019/5236* (2013.01); *A61B 2019/5238* (2013.01); *A61B 2019/5251* (2013.01); *A61B 2019/5272* (2013.01); *A61B 2019/5458* (2013.01); *A61B 2034/2072* (2016.02)

(58) Field of Classification Search
CPC .... A61B 5/0422; A61B 5/062; A61B 5/6859; A61B 2019/5475; A61B 1/05
USPC ................... 600/374, 407; 606/41
See application file for complete search history.

(56) References Cited

U.S. PATENT DOCUMENTS

| | | | |
|---|---|---|---|
| 6,206,874 B1 | 3/2001 | Ubby et al. | |
| 6,318,375 B1 | 11/2001 | Plicchi et al. | |
| 6,428,561 B1 | 8/2002 | Johansson-Ruden et al. | |
| 6,690,963 B2 * | 2/2004 | Ben-Haim et al. | 600/424 |
| 7,099,712 B2 | 8/2006 | Fuimaono et al. | |
| 7,353,067 B1 | 4/2008 | Helland et al. | |
| 2005/0148837 A1 | 7/2005 | Fuimaono et al. | |
| 2005/0182393 A1 | 8/2005 | Abboud et al. | |
| 2010/0286791 A1 * | 11/2010 | Goldsmith | A61B 17/12022 623/23.7 |
| 2011/0190750 A1 | 8/2011 | Pageard | |
| 2012/0035584 A1 | 2/2012 | Thompson-Nauman et al. | |

FOREIGN PATENT DOCUMENTS

EP    2401980 A1    1/2012

OTHER PUBLICATIONS

European Search Report dated Feb. 21, 2014 for corresponding Application No. EP13194723.

* cited by examiner

*Primary Examiner* — Joel Lamprecht
(74) *Attorney, Agent, or Firm* — Louis J. Capezzuto

(57) ABSTRACT

An invasive medical probe includes an insertion tube, having a proximal end and a distal end configured for insertion into a body of a patient. Multiple arms extend distally from the distal end of the insertion tube. Each arm has a distal tip and includes a magnetic transducer and an adhesive element, which is configured to removably attach the distal tip to a tissue surface within the body.

22 Claims, 2 Drawing Sheets

LOCATION SENSING USING A LOCAL COORDINATE SYSTEM

FIELD OF THE INVENTION

The present invention relates generally to methods and devices for invasive medical treatment, and specifically to accurately sensing the location of a probe inside a body organ.

BACKGROUND

Magnetic position sensing is now widely used in tracking the location of a catheter in the heart, both for diagnostic purposes, such as mapping cardiac electrical activity, and therapeutic, such as ablation of arrhythmogenic tissue. This type of position sensing is implemented in the CARTO® system, produced by Biosense Webster Inc. (Diamond Bar, Calif.).

A magnetic position sensing system of this sort is described, for example, in U.S. Pat. No. 6,690,963, whose disclosure is incorporated herein by reference. The system is used for determining the location and orientation of an invasive medical instrument, such as a catheter or endoscope, relative to a reference frame. It comprises a plurality of field generators, which generate known, distinguishable fields, preferably continuous AC magnetic fields, in response to drive signals. A plurality of sensors are situated in the invasive medical instrument proximate the distal end thereof and generate sensor signals in response to the fields. A signal processor has an input for a plurality of signals corresponding to the drive signals and the sensor signals and produces three location coordinates and three orientation coordinates of a point on the invasive medical instrument.

Catheters having multiple, trackable arms are also known in the art. For example, U.S. Pat. No. 7,099,712, whose disclosure is incorporated herein by reference, describes such a catheter for mapping the electrical activity in a heart. The catheter comprises a plurality of spines, each capable of obtaining electrical, mechanical and locational data. Each spine comprises at least one location sensor and at least one electrode, preferably a tip electrode and at least one ring electrode. The spines may be arranged in an expanded arrangement, wherein each spine extends radially outwardly from the catheter body, or in a collapsed arrangement, wherein each spine is disposed generally along the longitudinal axis of the catheter body. In use, at least one electrode from each spine is positioned in contact with heart tissue to map the electrical activity of the heart. The location sensors are used to determine the location of each point where the electrical activity is monitored.

SUMMARY

Embodiments of the present invention provide apparatus and methods that enhance the accuracy of tracking the location of an invasive probe relative to the organ in which the probe is located.

There is therefore provided, in accordance with an embodiment of the present invention, an invasive medical probe, which includes an insertion tube, having a proximal end and a distal end configured for insertion into a body of a patient. Multiple arms extend distally from the distal end of the insertion tube, each arm having a distal tip and including a magnetic transducer and an adhesive element, which is configured to removably attach the distal tip to a tissue surface within the body.

The magnetic transducer may include one or more coils.

In one embodiment, the adhesive element is configured to extrude a biocompatible glue via the distal tip in order to attach the distal tip to the tissue surface. In another embodiment, the adhesive element is configured to chill the distal tip so as to attach the distal tip to the tissue surface by cryoadhesion.

Typically, the arms are movable between a collapsed arrangement, in which the arms are disposed along a longitudinal axis of the insertion tube, and an expanded arrangement, in which the arms are spread radially apart so as to contact the tissue surface at different, respective locations.

In a disclosed embodiment, the insertion tube is configured for insertion into a chamber of a heart of the patient, and the adhesive element of each arm is configured to removably attach the distal tip to endocardial tissue.

There is also provided, in accordance with an embodiment of the present invention, a medical system, which includes a reference probe, including an insertion tube, having a proximal end and a distal end configured for insertion into an organ in a body of a patient, and including multiple arms extending distally from the distal end of the insertion tube. The arms have respective distal tips and include respective first magnetic transducers and adhesive elements, which are configured to removably attach the distal tips to respective locations on a tissue surface within the organ, thereby defining an organ frame of reference. An operational probe is configured for insertion into the organ in a vicinity of the reference probe and includes a second magnetic transducer and at least one functional element. A control unit is configured to drive the magnetic transducers in the arms and in the operational probe to transmit and receive magnetic fields, and is coupled to receive and process signals from the magnetic transducers in response to the magnetic fields so as to compute position coordinates of the operational probe in the organ frame of reference.

In some embodiments, the magnetic fields transmitted by the magnetic transducers are first magnetic fields, and the signals received by the control unit in response to the first magnetic fields are first signals, wherein the system includes a plurality of field generators, which are configured to generate respective second magnetic fields from respective locations outside a body of a patient, the locations defining a fixed frame of reference, and wherein the control unit is coupled to receive and process second signals from the first magnetic transducers in response to the second magnetic fields in order to compute respective coordinates of the arms in the fixed frame of reference.

The control unit may be coupled to register the organ frame of reference relative to the fixed frame of reference based on the respective coordinates of the distal tips. Additionally or alternatively, the control unit may be configured to drive the first magnetic transducers to transmit the first magnetic fields and is configured to receive the first signals from the second magnetic transducer in response to the first magnetic fields.

In a disclosed embodiment, the functional element includes at least one electrode. Typically, the control unit is configured to track the position coordinates of the operational probe in the organ frame of reference, responsively to the signals, while the operational probe moves within the organ in the course of a medical procedure carried out by the operational probe.

There is additionally provided, in accordance with an embodiment of the present invention, a method for performing a medical procedure, which includes inserting a reference probe into an organ in a body of a patient, the probe including an insertion tube and multiple arms extending distally from a distal end of the insertion tube, wherein the arms have respective distal tips and include respective first magnetic transducers. The distal tips of the arms are removably attached to respective locations on a tissue surface within the organ, thereby defining an organ frame of reference. An operational probe, including a second magnetic transducer, is inserted into the organ in a vicinity of the reference probe. The magnetic transducers in the arms and the operational probe are driven to transmit and receive magnetic fields. Signals from the magnetic transducers in response to the magnetic fields are received and processed so as to compute position coordinates of the operational probe in the organ frame of reference.

The present invention will be more fully understood from the following detailed description of the embodiments thereof, taken together with the drawings in which:

DETAILED DESCRIPTION OF EMBODIMENTS

Figure 1:
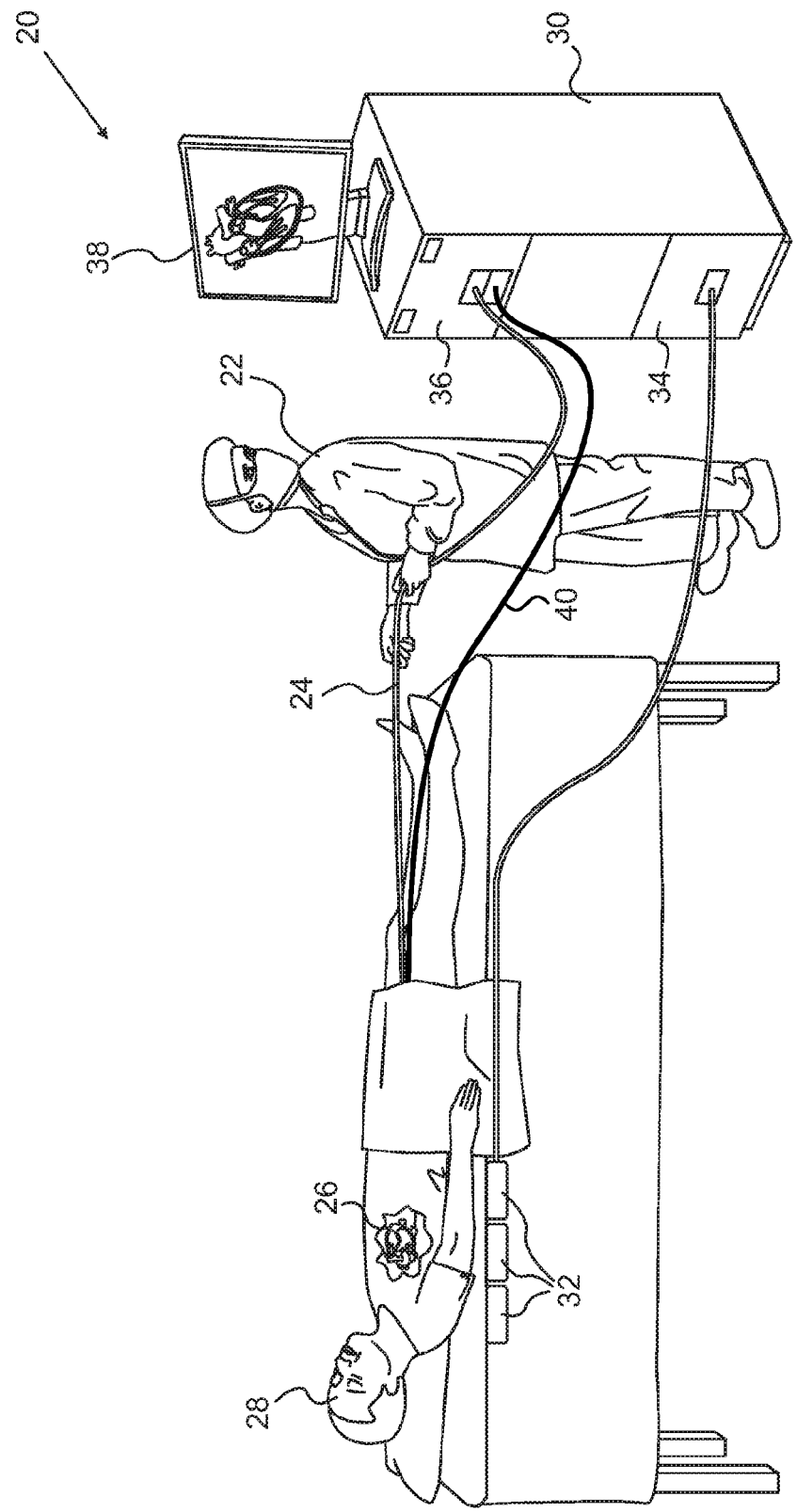
FIG. 1 is a schematic, pictorial illustration of a system for cardiac catheterization, in accordance with an embodiment of the present invention.

Tracking of an invasive probe, such as a catheter, relative to a body organ in which the probe is located can be difficult, especially if the organ moves as a whole within the body, or if the organ has its own internal movement. The heart, for example, has both types of movement, since in addition to beating, it has some freedom to move within the chest of a subject, while the chest as a whole moves due to respiration. On the other hand, in catheter tracking systems that are known in the art, such as the above-mentioned CARTO system, the catheter position is typically tracked in the frame of reference of field generators in fixed locations outside the body.

Various methods have been used to compensate for heart movement in order to derive the actual position of the catheter relative to the heart. The position of the heart may be measured directly, for example by magnetic resonance imaging (MRI). Alternatively or additionally, a reference catheter may be placed and held stationary at a particular anatomical feature in the heart, such as the coronary sinus, to give a reference position reading to which the position of the moving catheter can be compared. The reference catheter, however, is prone to instability and typically indicates movement only of the heart as a whole.

Embodiments of the present invention adopt a different approach, using a novel reference probe to establish an organ frame of reference, which is tied to the position of the heart itself and inherently compensates for heart movement. The reference probe comprises an insertion tube with multiple arms extending distally from its distal end. Each arm comprises a magnetic transducer (such as one or more miniature coils) and has an adhesive element for removably attaching the distal tip of the arm to a tissue surface within the body. The adhesive element may comprise, for example, a tube that extrudes a suitable biocompatible glue, or a cryogenic element, which chills the distal tip sufficiently to cause cryo-adhesion to the tissue surface. After the procedure, the arms are released from the tissue surface by dissolving the glue or allowing the tips of the arms to re-warm, for example.

An operational probe, having its own magnetic transducer, is inserted into the heart in the vicinity of the reference probe, and a functional element (such as an electrode) at the distal end of the operational probe is used to perform a medical procedure, which may be diagnostic and/or therapeutic. A control unit drives the magnetic transducers in the arms and in the operational probe to transmit and receive magnetic fields, either from the arms to the operational probe or from the operational probe to the arms. The control unit receives and processes the signals that are generated by the receiving transducer or transducers in response to this magnetic field, and thus computes position coordinates of the operational probe in the organ frame of reference.

The organ frame of reference may optionally be referred to an external, fixed frame of reference that is defined by magnetic field generators at respective locations outside the patient's body of a patient. The magnetic transducers in the arms of the reference probe sense the fields generated by these field generators, while the arms are attached to the tissue surface. The control unit receives and processes the signals generated by these magnetic transducers in response to the magnetic fields of the field generators, and thus computes the respective coordinates of the distal tips of the arms in the fixed frame of reference. In this manner, the control unit is able to register the organ frame of reference relative in the fixed frame of reference, based on the respective positions of the distal tips.

In the embodiments that are described below, the reference probe and operational probe are described as cardiac catheters and are used in procedures that are performed in the heart. The principles of the present invention, however, are not limited to this specific context, but may rather be applied to other body organs and to probes and procedures that may be used in such organs.

Figure 2:
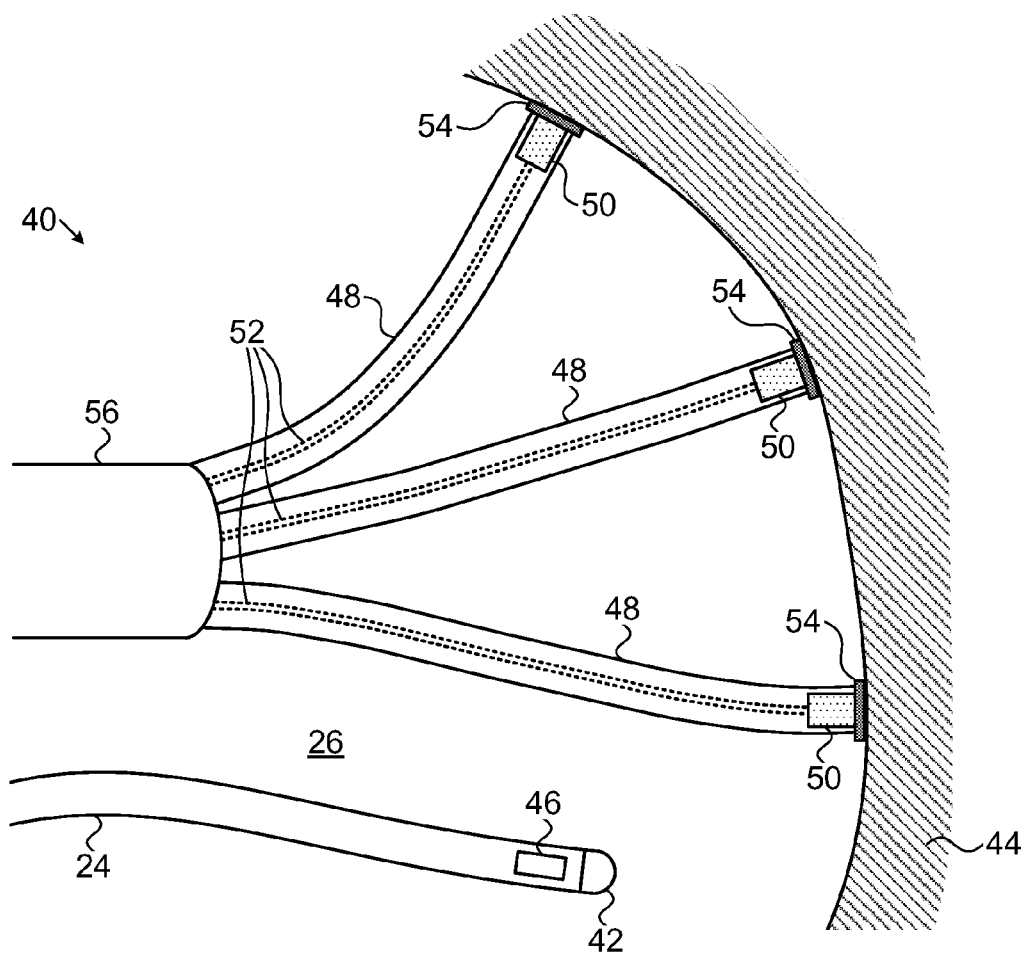
FIG. 2 is a schematic, sectional view of a heart chamber into which catheters are inserted, in accordance with an embodiment of the present invention.

FIG. 1 is a schematic pictorial illustration of a system 20 for invasive treatment of a heart 26 of a patient 28, in accordance with an embodiment of the present invention. An operator 22, such as a cardiologist, inserts flexible probes, such as catheters 24 and 40, through the vascular system of patient 28 so that the distal ends of the catheters enter a chamber of the patient's heart. Operator 22 advances the catheters so that their distal tips engage endocardial tissue at desired locations (as shown in FIG. 2). Catheter 24 is configured as a operational catheter, with a function element, such as an electrode, for performing desired diagnostic and/or therapeutic functions in heart 26. Catheter 40 serves as a reference catheter, for use in finding the location of catheter 24 in the frame of reference of the heart.

Catheters 24 and 40 are connected by suitable connectors (not shown) at their proximal ends to a console 30. The console comprises a control unit 36, which sends and receives signals to and from catheters 24 and 40 in order to control and monitor their operations. For example, the control unit may apply electrical energy to catheter 24 in order to ablate tissue in heart 26 and/or may receive electrical signals from the catheter in order to measure cardiac electrical activity. Alternatively or additionally, catheter 24 may be used for other diagnostic and/or therapeutic functions, as are known in the art. In addition, control unit 36 drives magnetic transducers at the distal ends of catheters 24 and 40 (as shown in FIG. 2) to transmit and receive magnetic fields, and processes signals from the magnetic transducers in response to the magnetic fields so as to compute position coordinates of catheter 24 in a frame of reference that moves with the heart, as described below.

In the pictured embodiment, system 20 uses magnetic position sensing to determine position coordinates of reference catheter 40 inside heart 26 relative to a fixed frame of reference. To determine the position coordinates, a driver circuit 34 in console 30 drives field generators 32 to generate magnetic fields within the body of patient 28. Typically, field generators 32 comprise coils, which are placed below the patient's torso at known positions external to the body. These coils generate magnetic fields in a predefined working volume that contains heart 26. The magnetic transducers within the end section of catheter 40 (as shown in FIG. 2) output electrical signals in response to these magnetic fields. Control unit 36 processes these signals in order to determine position (location and/or orientation) coordinates of multiple arms extending from the distal end of catheter 40, as explained below. Console 30 may use the coordinates of catheters 24 and 40 in driving a display 38, particularly to show the location and status of catheter 24.

The term "magnetic transducer," as used in the context of the present description and in the claims, refers to an element that converts electrical signals to magnetic fields and/or vice versa. In other words, when a suitable electrical driving signal is applied to a magnetic transducer, it causes the magnetic transducer to generate a magnetic field; and an appropriate magnetic field in the area of a magnetic transducer will cause the magnetic transducer to output an electrical signal. Wire coils are one example of a magnetic transducer, but other sorts of devices, such as solid-state transducers, may also be used for this purpose. Methods of magnetic position sensing and processing that may be applied by control unit 36 in finding the coordinates of catheters 24 and 40, using the magnetic transducers in the catheters, are described in detail, for example, in the above-mentioned U.S. Pat. No. 6,690,963 and are implemented in the above-mentioned CARTO system.

Although FIG. 1 shows a particular system configuration, other system configurations may be used in alternative embodiments of the present invention. For example, the methods described hereinbelow may be applied using position transducers of other types, such as impedance-based or ultrasonic position sensors. The term "position transducer" as used herein refers to an element that causes console 30 to receive signals indicative of the coordinates of the element. The position transducer may thus comprise a receiver in the catheter, which generates a position signal to the control unit based on energy received by the transducer; or it may comprise a transmitter, emitting energy that is sensed by a receiver external to the probe. Furthermore, the methods described hereinbelow may similarly be applied in diagnostic and therapeutic applications using not only catheters, but also invasive probes of other types, both in the heart and in other body organs and regions.

FIG. 2 is a schematic, sectional view of a chamber of heart 26 into which catheters 24 and 40 have been inserted, in accordance with an embodiment of the present invention. Operational catheter 24 comprises a functional element, such as an electrode 42, at its distal tip. The electrode is brought into contact with the surface of endocardial tissue 44 and may be used to sense tissue electrical activity or to ablate tissue 44 for treatment of arrhythmias, for example. Alternatively or additionally, catheter 24 may comprise multiple electrodes or functional elements of other suitable type that is known in the art, such as an ultrasonic transducer. Catheter 24 also comprises a magnetic transducer 46, such as a miniature coil or a set of orthogonal coils, as described in the above-mentioned U.S. Pat. No. 6,690,963.

Reference catheter 40 comprises an insertion tube 56, with multiple arms 48 extending distally from the distal end of the insertion tube. Although three arms are shown in FIG. 2, catheter 40 may alternatively comprise a larger number of arms. For ease of insertion through the vascular system and into the heart, arms 48 may be movable between a narrow, collapsed arrangement, in which the arms are disposed along the longitudinal axis of the insertion tube, and an expanded arrangement, in which the arms are spread radially apart, as shown in FIG. 2. For example, during insertion, arms 48 may be retracted into the distal end of insertion tube 56, and may then be extended outward once the insertion tube is inside the target heart chamber. The arms may contain resilient reinforcing struts, as described in the above-mentioned U.S. Pat. No. 7,099,712, which cause them to spread apart so as to contact the tissue surface at locations that are spaced apart.

The distal tip of each arm 48 contains a magnetic transducer 50 (which may be of a similar type to transducer 46) and an adhesive element, whose purpose is to removably attach the distal tip to the surface of endocardial tissue 44. In the pictured example, the adhesive element comprises a tube 52, which extrudes a suitable biocompatible glue via the distal tip in order to create a temporary adhesive pad 54, thus attaching the distal tip to the tissue surface. Biocompatible glues that may be used for this purpose are described, for example, in U.S. Pat. No. 6,428,561, whose disclosure is incorporated by reference. Optionally, upon completion of the procedure, a suitable biocompatible solvent may be extruded through the distal tips of arms 48 to dissolve the glue. This solvent may be extruded through tubes 52 or from a separate tube or reservoir (not shown).

Alternatively, arms 48 may comprise other sorts of adhesive elements. For example, the adhesive element may comprise a cryogenic member, which chills the distal tip sufficiently to cause the distal tip to adhere to the tissue surface by cryo-adhesion. A cryogenic member that may be used in a catheter, and may thus be adapted to serve as an adhesive element in catheter 40, is described, for example, in U.S. Patent Application Publication 2012/0035584, whose disclosure is incorporated herein by reference.

After arms 48 have been extended from insertion tube, magnetic transducers 50 sense the magnetic fields produced by field generators 32 and output signals to control unit 36. These signals enable the control unit to find the coordinates of each arm 48 in the fixed frame of reference of field generators 32. Before activating the adhesive elements to fix the arms in place, operator 22 and/or control unit 36 may verify that the distal tips are in firm contact with the surface of tissue 44. Such contact may be verified, for example, by MRI or fluoroscopic imaging. Alternatively or additionally, a sensor (not shown) in each arm may be used to verify good contact. For example, an electrode at the tip of each arm can be used to verify contact by measuring electrical impedance between the arm and the tissue, or a force sensor in each arm can sense the force exerted between the arm and the tissue.

Once proper contact between arms 48 and tissues has been made and, if desired, verified, the adhesive elements are activated and fix the arms in place. The location coordinates of transducers 50 in the arms are known, relative to an external, fixed frame of reference, on the basis of sensing the magnetic fields of field generators 32. As a result of the adhesive elements, once arms 48 have been suitably positioned in contact with the heart wall and fixed in place, operator 22 can be confident that the arms will not move during the procedure. Thus, the arms establish a heart frame of reference that will stably track the movement of the heart, while maintaining registration with the fixed frame of reference of the external field generators.

To find the coordinates of catheter 24 in the heart frame of reference, control unit 36 changes the role of magnetic transducers 50 from field sensors to field generators and drives transducers 50 to generate magnetic fields. Magnetic transducer 46 in catheter 24 outputs signals in response to these fields, and control unit 36 processes these signals in order to find the coordinates of catheter 24 in the heart frame of reference. The control unit is thus able to track and display the location of catheter 24 relative to the heart itself. Because transducers 46 and 50 are in mutual proximity, it is sufficient for transducers 50 to generate relatively weak magnetic fields in order for transducer to sense the fields, and the currents needed to drive transducers 50 are thus much smaller than the driving currents of field generators 32.

Alternatively, control unit 36 may drive transducer 46 to generate a magnetic field, which will be received and sensed by transducers 50. Control unit 36 may process these signals in an equivalent manner to that described above in order to find the position coordinates of catheter 24 in the heart frame of references.

In either of the above configurations, control unit 36 may periodically sample signals output by magnetic transducers 50 in arms 48 in response to the fields of field generators 32, in order to verify and register the locations of the arms (and of the corresponding heart frame of reference) in the fixed frame of reference of the field generators.

Alternatively, in some embodiments, field generators 32 may be used only for initial positioning, or may not be used at all. For example, reference catheter 40 may be inserted into heart 26, and arms 48 may be brought into contact with and attached to tissue 44 under fluoroscopic or MRI visualization. The locations of transducers 50 in arms 48 may thus be registered with a current or pre-acquired image of the heart. Control unit then drives transducers 50 to generate magnetic fields, as described above, and processes the signals from transducer 46 in order to find the coordinates of catheter 24 in a heart coordinate system. This heart coordinate system may be registered with the image (with or without use of field generators 32), or system 20 may operate without performing any sort of registration of the heart coordinate system established by arms 48.

As another alternative (not shown in the figures) one or more of the magnetic transducers that are used to generate magnetic fields in the heart and thus establish the heart coordinate system may be fixed externally to the heart.

Although the embodiment shown in FIG. 2 relates to a particular type and configuration of operational catheter 24, the principles of the present invention may similarly be applied in tracking catheters of other types, as well as in tracking multiple operational catheters simultaneously. Furthermore, as noted earlier, these principles may similarly be applied in tracking the locations of probes in other body organs. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An invasive medical probe for performing a medical procedure on a body of a patient, the probe comprising:
   an insertion tube, having a proximal end and a distal end configured for insertion into a body of a patient; and
   multiple arms extending distally from the distal end of the insertion tube, each arm having a distal tip and comprising:
      a magnetic transducer; and
      an adhesive element, which is configured to removably attach the distal tip to a tissue surface of a moveable organ within the body, the adhesive element being configured to create a temporary adhesive pad for temporarily fixing the distal tip of each arm to the tissue surface of the moveable organ for permitting the medical probe to be used to perform the medical procedure, wherein the temporary adhesive pad is configured to allow the multiple arms and the insertion tube of the medical probe to be removed from the moveable organ and from the body of the patient upon completion of the medical procedure.

2. The probe according to claim 1, wherein the magnetic transducer comprises one or more coils.

3. The probe according to claim 1, wherein the adhesive element is configured to extrude a biocompatible glue via the distal tip in order to attach the distal tip to the tissue surface.

4. The probe according to claim 1, wherein the adhesive element is configured to chill the distal tip so as to attach the distal tip to the tissue surface by cryo-adhesion.

5. The probe according to claim 1, wherein the arms are movable between a collapsed arrangement, in which the arms are disposed along a longitudinal axis of the insertion tube, and an expanded arrangement, in which the arms are spread radially apart so as to contact the tissue surface at different, respective locations.

6. The probe according to claim 1, wherein the insertion tube is configured for insertion into a chamber of a heart of the patient, and wherein the adhesive element of each arm is configured to removably attach the distal tip to endocardial tissue.

7. A medical system for performing a medical procedure on a body of a patient, the system comprising:
   a reference probe, comprising an insertion tube, having a proximal end and a distal end configured for insertion into a moveable organ in a body of a patient, and comprising multiple arms extending distally from the distal end of the insertion tube,
   wherein the arms have respective distal tips and comprise respective first magnetic transducers and adhesive elements, which are configured to removably attach the distal tips to respective locations on a tissue surface within the organ, thereby defining an organ frame of reference for the moveable organ, the adhesive elements being configured to create a temporary adhesive pad for temporarily fixing the distal tips of each arm to the respective locations of the tissue surface of the moveable organ and for permitting the medical probe to be used to perform the medical procedure, wherein the temporary adhesive pad is configured to allow the multiple arms and the insertion tube of the medical probe to be removed from the moveable organ and from the body of the patient upon completion of the medical procedure;
   an operational probe, configured for insertion into the organ in a vicinity of the reference probe and comprising a second magnetic transducer and at least one functional element; and
   a control unit, which is configured to drive the magnetic transducers in the arms and in the operational probe to transmit and receive magnetic fields, and which is coupled to receive and process signals from the magnetic transducers in response to the magnetic fields so as to compute position coordinates of the operational probe in the organ frame of reference.

8. The system according to claim 7, wherein the magnetic fields transmitted by the magnetic transducers are first magnetic fields, and the signals received by the control unit in response to the first magnetic fields are first signals, and
   wherein the system comprises a plurality of field generators, which are configured to generate respective second magnetic fields from respective locations outside a body of a patient, the locations defining a fixed frame of reference, and wherein the control unit is coupled to receive and process second signals from the first magnetic transducers in response to the second magnetic fields in order to compute respective coordinates of the arms in the fixed frame of reference.

9. The system according to claim 8, wherein the control unit is coupled to register the organ frame of reference relative to the fixed frame of reference based on the respective coordinates of the distal tips.

10. The system according to claim 8, wherein the control unit is configured to drive the first magnetic transducers to transmit the first magnetic fields and is configured to receive the first signals from the second magnetic transducer in response to the first magnetic fields.

11. The system according to claim 7, wherein the functional element comprises at least one electrode.

12. The system according to claim 7, wherein the control unit is configured to track the position coordinates of the operational probe in the organ frame of reference, responsively to the signals, while the operational probe moves within the organ in the course of a medical procedure carried out by the operational probe.

13. The system according to claim 7, wherein the reference probe and operational probe are configured for insertion into a chamber of a heart of the patient, and wherein the adhesive element of each arm is configured to removably attach the distal tip to endocardial tissue.

14. A method for performing a medical procedure, comprising:

inserting a reference probe into a moveable organ in a body of a patient, the probe comprising an insertion tube and multiple arms extending distally from a distal end of the insertion tube, wherein the arms have respective distal tips comprising an adhesive element being configured to create a temporary adhesive pad for temporarily fixing the distal tip of each arm to the tissue surface of the moveable organ, the arms each comprising respective first magnetic transducers, the temporary adhesive pad being configured to allow the multiple arms and the insertion tube of the reference probe to be removed from the moveable organ and from the body of the patient upon completion of the medical procedure;

removably attaching the distal tips of the arms to respective locations on a tissue surface within the moveable organ, thereby defining an organ frame of reference;

inserting an operational probe, comprising a second magnetic transducer, into the organ in a vicinity of the reference probe;

driving the magnetic transducers in the arms and the operational probe to transmit and receive magnetic fields; and receiving and processing signals from the magnetic transducers in response to the magnetic fields so as to compute position coordinates of the operational probe in the organ frame of reference; and removing the reference probe from the moveable organ and from the body of the patient upon completion of the medical procedure.

15. The method according to claim 14, wherein receiving and processing the signals comprises tracking the position coordinates of the operational probe in the organ frame of reference, responsively to the signals, while moving the operational probe within the organ in the course of the medical procedure.

16. The method according to claim 14, wherein moving the operational probe comprises bringing an electrode on the operational probe into contact with multiple points on the tissue surface in the organ.

17. The method according to claim 14, and comprising releasing the distal tips from the respective locations on the tissue surface upon completion of the medical procedure.

18. The method according to claim 17, wherein removably attaching the distal tips comprises extruding a biocompatible glue from the distal tips, and wherein releasing the distal tips comprises extruding a biocompatible solvent to dissolve the glue.

19. The method according to claim 14, wherein removably attaching the distal tips comprises chilling the distal tip so as to attach the distal tip to the tissue surface by cryo-adhesion.

20. The method according to claim 14, wherein driving the magnetic transducers comprises generating first magnetic fields, and the signals received from the magnetic transducers in response to the first magnetic fields are first signals, and wherein the method comprises generating second magnetic fields from respective locations outside a body of a patient, the locations defining a fixed frame of reference, and receiving and processing second signals from the first magnetic transducers in response to the second magnetic fields in order to compute respective coordinates of the arms in the fixed frame of reference.

21. The method according to claim 20, and comprising registering the organ frame of reference relative to the fixed frame of reference based on the respective coordinates of the distal tips.

22. The method according to claim 14, wherein inserting the reference probe and the operational probe comprises introducing the reference probe and the operational probe into a chamber of a heart of the patient, and wherein removably attaching the distal tips comprises attaching the distal tips to endocardial tissue.

* * * * *